US005912235A

United States Patent [19]

Hoeltje et al.

[11] Patent Number: 5,912,235

[45] Date of Patent: Jun. 15, 1999

[54] 10, 13, 15-TRIOXATRICYCLO [9.2.1.1.$^{9,6}$]-PENTADECAN ONE DERIVATIVES, METHOD FOR THEIR PRODUCTION AND PHARMACEUTICAL COMPOSITIONS CONTAINING THEM

[75] Inventors: Dagmar Hoeltje, Gehrden; Ulf Preuschoff, Uelzen/Oldenstadt; Christian Eeckhout, Lindwedel; Emil Finner, Isernhagen, all of Germany

[73] Assignee: Solvay Pharmaceuticals GmbH, Hannover, Germany

[21] Appl. No.: 08/954,891

[22] Filed: Oct. 21, 1997

[30] Foreign Application Priority Data

Oct. 24, 1996 [DE] Germany .......................... 196 44 195

[51] Int. Cl.$^{6}$ ............................ A61K 31/70; C07H 1/00; C07H 17/08

[52] U.S. Cl. ............................ 514/28; 536/7.1; 536/7.2; 536/18.1; 536/18.5

[58] Field of Search .................................. 536/7.2, 18.1, 536/18.5, 7.1; 574/28

[56] References Cited

U.S. PATENT DOCUMENTS 3,725,385 4/1973 Freiberg .................................. 536/7.1

5,418,224 5/1995 Hoeltje et al. ........................... 514/28

*Primary Examiner*—Elli Peselev

*Attorney, Agent, or Firm*—Evenson, McKeown, Edwards & Lenahan, P.L.L.C.

[57] ABSTRACT

Ring-contracted N-demethyl-N-isopropyl-erythromycin-A-spiroacetal compounds corresponding to formula I

I $R^1$ N—$CH(CH_3)_2$ HO $H_3C$ $CH_3$ O O $H_3C$ O $CH_3$ O $CH_3$ $CH_3$ $H_3C$ OH H O $CH_3$ O $OCH_3$ O $CH_3$ O OH $CH_3$ having gastrointestinally effective motilin-agonistic properties and the preparation thereof.

8 Claims, No Drawings

10, 13, 15-TRIOXATRICYCLO [9.2.1.1.$^{9.6}$]-PENTADECAN ONE DERIVATIVES, METHOD FOR THEIR PRODUCTION AND PHARMACEUTICAL COMPOSITIONS CONTAINING THEM

BACKGROUND OF THE INVENTION

The present invention relates to novel N-substituted [(1'R),2R,3S,4S,5R,6R,9R,11R,12R,14R]-11-(1'-hydroxypropyl)-3-[(2,6-dideoxy-3-C-methyl-3-0-methyl-α-L-ribohexopyranosyl)-oxy]-5-[(3,4,6-trideoxy-3-amino-β-D-xylohexopyranosyl)-oxy]-2,4,6,8,11,14-hexamethyl-10,13,15-trioxatricyclo[9.2.1.1.$^{9.6}$]-pentadecan-1-one compounds with motilin-agonistic properties and to the acid addition salts thereof and to pharmaceutical formulations containing these compounds and to methods for the preparation of these compounds. The compounds according to the invention are ring-contracted N-demethyl-N-isopropyl-spiroacetal derivatives of erythromycin A.

The antibiotic erythromycin A is known to have, in addition to its antibiotic effects, also gastrointestinal side effects which are undesirable for antibiotics, inter alia a great increase in the contraction activity in the gastrointestinal region with gastric and intestinal cramps, nausea, vomiting and diarrhea.

There have been several attempts to modify erythromycin A to obtain derivatives in which the antibiotic effect is virtually no longer present but an effect influencing the motility of the gastrointestinal tract is obtained. U.S. Pat. No. 5,418,224 (=EP 550,895) discloses ring-contracted N-demethyl-N-isopropyl-erythromycin A derivatives having gastrointestinally effective motilin-agonistic properties.

SUMMARY OF THE INVENTION

The object of the present invention is to provide novel, orally-effective ring-contracted derivatives of erythromycin A without an antibiotic effect and with properties having a beneficial effect on the motility of the gastrointestinal tract with a better activity profile.

This and other objects have been achieved in accordance with the present invention by providing a [(1'R),2R,3S,4S,5R,6R,9R,11R,12R,14R]-11-(1'-hydroxypropyl)-2,4,6,8,11,14-hexamethyl-10,13,15-trioxatricyclo[9.2.1.1$^{9.6}$]-pentadecan-1-one compound corresponding to formula I:

I

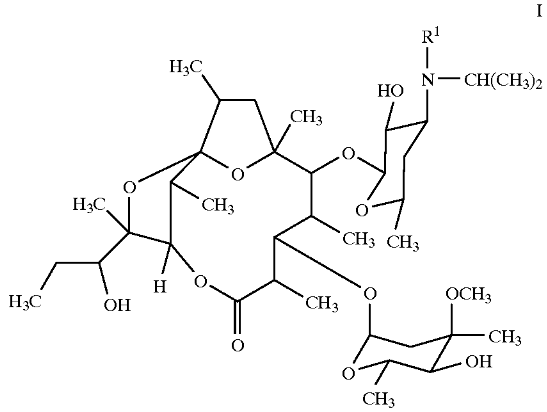

wherein $R^1$ denotes methyl or hydrogen, or a stable and physiologically acceptable acid addition salt thereof.

In accordance with a further aspect of the invention, the objects have been achieved by providing a method of preparing a [(1'R),2R,3S,4S,5R,6R,9R,11R,12R,14R]-11-(1'-hydroxypropyl)-2,4,6,8,11,14-hexamethyl-10,13,15-trioxatricyclo[9.2.1.1$^{9.6}$]-pentadecan-1-one compound corresponding to formula I:

I

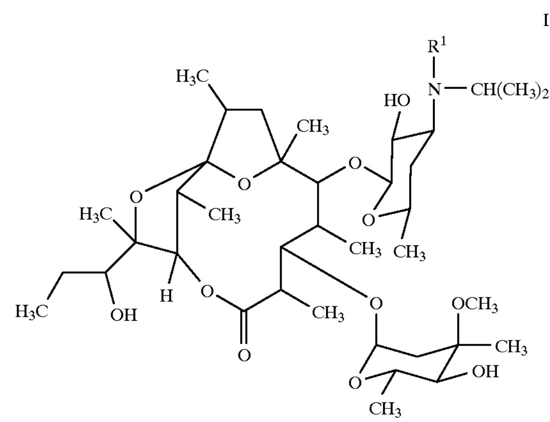

wherein $R^1$ denotes methyl or hydrogen, comprising treating a [2R(2'R,3'R),3S,4S,5R,6R,10R,11R]-11-(2',3'-dihydroxypent-2'-yl)-2,4,6,8,10-pentamethyl-12,13-dioxabicyclo[8.2.1]-tridec-8-en-1-one compound corresponding to formula II:

II

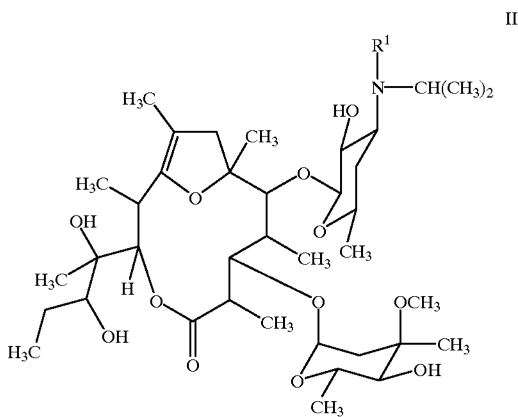

wherein $R^1$ has the above meaning, with acid to effect ring closure and convert the compound of formula II into a compound of Formula I.

DESCRIPTION OF PREFERRED EMBODIMENTS

It has now been found that the novel ring-contracted N-demethyl-N-isopropyl-spiroacetal derivatives of erythromycin A have selective motilin-agonistic properties and stimulate the motility of the gastrointestinal tract in a beneficial way and show effects enhancing the tone of the lower oesophagus sphincter and the tone of the stomach. Because of their activity profile, the substances according to the invention are suitable for the treatment of motility disturbances in the gastrointestinal tract and moreover are distinguished by being well tolerated, having good oral effectiveness and good-stability.

The present invention therefore relates to novel [(1'R),2R,3S,4S,5R,6R,9R,11R,12R,14R]-11-(1'-hydroxypropyl)-2,4,6,8,11,14-hexamethyl-10,13,15-trioxatricyclo

[9.2.1.1$^{9,6}$]-pentadecan-1-one derivatives of the general formula I

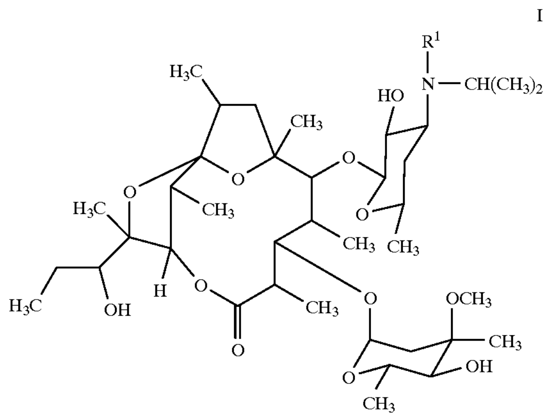

in which $R^1$ denotes methyl or hydrogen, and to the stable and physiologically tolerated acid addition salts thereof. The compound of Formula I in which $R^1$ is methyl has proved particularly beneficial.

The compounds of Formula I can be obtained by converting [2R(2'R,3'R),3S,4S,5R,6R,10R,11R]-11-(2',3'-dihydroxypent-2'-yl)-2,4,6,8,10-pentamethyl-12,13-dioxabicyclo[8.2.1]-tridec-8-en-1-one derivatives of the general formula II

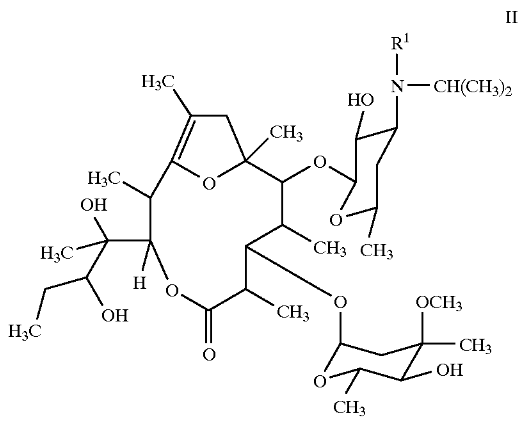

in which $R^1$ has the above meaning, by acid treatment in a known manner into compounds of Formula I and, if desired, introducing a methyl radical $R^1$ into the resulting compound of Formula I in which $R^1$ denotes hydrogen, or cleaving off the methyl radical $R^1$ in the resulting compound of Formula I in which $R^1$ denotes methyl, and, if desired, converting free compounds of Formula I into their stable acid addition salts, or converting the acid addition salts into the free compounds of Formula I.

The compounds of Formula I are obtained from compounds of Formula II by proton-catalyzed intramolecular spirocyclization. The spirocyclization is effected in known manner by treatment with acids, preferably in aqueous medium, at relatively low pH values, for example pH values of at most pH 3, advantageously at pH values of between 1.5 and 3. Water-soluble inorganic or organic acids which are inert to the other functional groups of the compounds of Formula I and II may be used as acids. It is desirable to avoid the pH value dropping below 1, so that no secondary hydrolysis reactions occur. Suitable reaction media are, for example, aqueous hydrochloric acid solution or aqueous acetic acid solution. Advantageously the cyclization reaction may be carried out in aqueous hydrochloric acid solution at room temperature.

The resulting compound of Formula I in which $R^1$ denotes hydrogen can, if desired, subsequently be alkylated in known manner to give the corresponding N-methyl compound. The alkylation can take place in known manner by reaction with a methyl halide or as reductive alkylation by reaction with formaldehyde under reducing conditions, and can be carried out, for example, under the conditions indicated below for the alkylation of the compounds of Formula III.

The methyl group $R^1$ can, if desired, subsequently be cleaved off from the compound of Formula I in which $R^1$ denotes methyl. The demethylation can be effected in known manner by treating the compound with a halogen, in particular iodine and/or bromine, in an inert solvent in the presence of a suitable base. Suitable bases include, for example, alkali metal alcoholates, alkali metal hydroxides and alkali metal salts of weak organic acids.

The compounds of Formula I can be isolated from the reaction mixture and purified in known manner. Acid addition salts can be converted in conventional manner into the free bases, and the latter can, if desired, be converted in known manner into pharmacologically acceptable acid addition salts. To avoid secondary hydrolysis reactions, it is desirable to use only equivalent amounts of acids for the salt formation.

Examples of suitable pharmacologically acceptable acid addition salts of the compounds of Formula I include the salts thereof with inorganic acids, for example carbonic acid, hydrohalic acids, especially hydrochloric acid, or with organic acids, for example lower aliphatic mono- or dicarboxylic acids such as maleic acid, fumaric acid, lactic acid, tartaric acid or acetic acid.

Two epimeric forms may occur at the asymmetric carbon produced by the spirocyclization reaction, the carbon atom in position 8, so that two isomers of the compounds of Formula I are possible. The present invention comprises both the mixture of isomers and the pure isomeric compounds of Formula I. An isomer mixture is produced upon the ring closure reaction. The pure isomers can be obtained from this mixture in known manner by conventional separation methods, for example by chromatographic separation.

The starting compounds of Formula II are known from U.S. Pat. No. 5,418,224, the disclosure of which is incorporated herein by reference, and can be prepared according to the methods described therein. Thus compounds of Formula II can be obtained by introducing an isopropyl group in known manner into compounds of the general Formula III The compounds of Formula III can be obtained using known methods, starting from erythromycin A of Formula IV

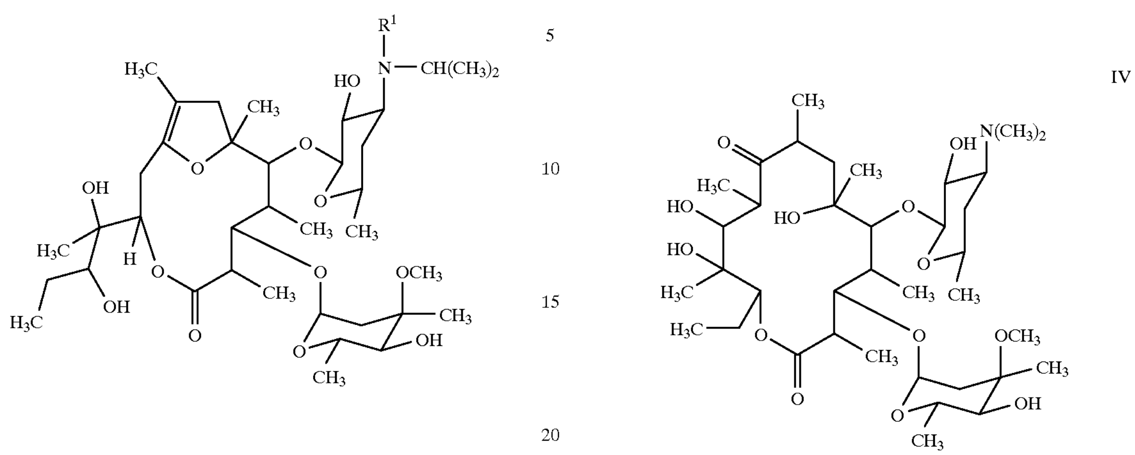

wherein $R^1$ has the above meaning.

To introduce the isopropyl group, the compounds of Formula III can be alkylated in known manner. Preferably the alkylation is performed as a reductive alkylation in a known manner by reacting the compound of Formula III with acetone under reducing conditions. For example, the compounds of Formula III can be reacted with acetone in the presence of a reduction agent, for example a complex borohydride compound such as sodium cyanoborohydride, sodium triacetoxyborohydride or sodium borohydride. If desired, the alkylation, in particular of that compound of Formula III in which $R^1$ is methyl, can also take place by reaction with an isopropyl halide, in particular isopropyl iodide, or isopropyl sulfate or an isopropyl sulfonic acid ester. Advantageously, the alkylation is carried out in an organic solvent which is inert under the reaction conditions. An excess of acetone, for example, may serve as solvent for the reductive alkylation. Furthermore, cyclic ethers, such as tetrahydrofuran or dioxane, aromatic hydrocarbons such as toluene, or alternatively lower alcohols, are also suitable solvents. The alkylation can be effected at temperatures between room temperature and the boiling temperature of the solvent. For alkylation with an isopropyl derivative, for example an isopropyl halide such as isopropyl iodide, one expediently operates in the presence of a base, such as, for example, an alkali metal carbonate or a tertiary organic amine.

If desired, a methyl radical $R^1$ can be introduced into a resulting compound of Formula II wherein $R^1$ is hydrogen, or the methyl radical $R^1$ can be cleaved off in a resulting compound of Formula II in which $R^1$ is methyl. Such methylation or demethylation operations can be performed in known manner, for example under the conditions described for the introduction or cleavage of a methyl group in the compounds of Formula I.

Thus, erythromycin A can initially be mono- or didemethylated by reaction with halogen, preferably iodine, in an inert solvent in the presence of a suitable base in known manner, for example by the method disclosed in U.S. Pat. No. 3,725,385 (=DE 2,154,032), the disclosure of which is incorporated herein by reference. Examples of suitable bases include alkali metal alcoholates, alkali metal hydroxides, alkali metal carbonates and alkali metal salts of weak carboxylic acids such as, for example, alkali metal acetates or propionates. One to ten equivalents of the halogen relative to the amount of erythromycin compound to be demethylated may be employed. Preferably alkali metal hydroxides and/or salts are used as bases for the monodemethylation. The amount of the base is preferably chosen so that a pH value in the range from 5 to 9 is ensured. Suitable solvents include methanol, cyclic ethers such as dioxane or tetrahydrofuran, dimethylformamide or mixtures of the said solvents with water. The monodemethylation is advantageously carried out at temperatures between room temperature and 50° C. The reaction can be promoted by irradiation with light, for example light having a wavelength of above 290 nm from a low pressure mercury lamp with a filter made of quartz or heat-resistant glass (for example Pyrex$^R$). The didemethylation is preferably carried out in a dry lower alcohol, e.g. methanol, in the presence of the corresponding alkali metal alcoholate at temperatures between 0 and 10° C. If desired, the preparation of the didemethylated product can also start from already monodemethylated product.

The mono- or didemethylated erythromycin A can be converted in known manner by mild acid treatment into a corresponding mono- or didemethylated 8,9-anhydroerythromycin A 6,9-hemiketal of the general formula V

V

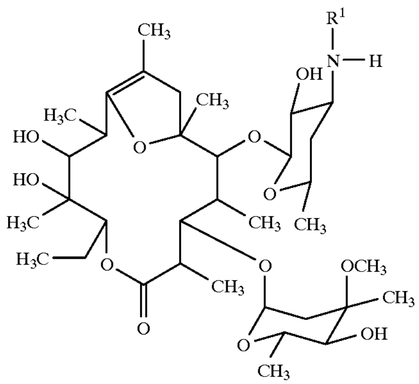

in which $R^1$ denotes hydrogen or methyl. The hemiketal formation can take place, for example, by treatment with an organic acid such as citric acid, formic acid or glacial acetic acid or dilute mineral acid at temperatures between room temperature and about 50° C.

A ring contraction of the 14-membered lactone ring of the erythromycin framework in the compounds of Formula V can be carried out in known manner by intramolecular translactonization to give a 12-membered lactone ring with formation of the corresponding compounds of Formula III. To do this, the compounds of Formula V are heated in known manner in a lower alcohol in the presence of a base, for example to temperatures between 40° C. and 70° C., preferably the boiling temperature of the reaction mixture. Particularly suitable bases include alkali metal carbonates, but organic bases such as tertiary amines, especially tertiary lower alkylamines, are also suitable. The configuration of the asymmetric centers does not change in this ring contraction.

The novel compounds of Formula I and the physiologically acceptable acid addition salts thereof have interesting pharmacological properties, especially motilin-agonistic properties stimulating the motility of the gastrointestinal tract. They are then characterized by a beneficial activity profile with good oral effectiveness. They are free of antibiotic effects and have a high selective affinity for motilin receptors, whereas in dose ranges with motilin-agonistic efficacy they show no practically relevant affinity for other receptors in the gastrointestinal tract such as adrenaline, acetylcholine, histamine, dopamine or serotonin receptors. The compounds exhibit a surprisingly good tolerance by the liver, which makes them suitable for administration over longer periods of time.

In the healthy state, the autonomic nervous system and hormones in the gastrointestinal tract cooperate to ensure controlled digestion of the consumed food and in order to generate a controlled contraction activity of the gastrointestinal tract not only immediately after intake of food but also when the gastrointestinal tract is empty. Motilin is a known gastrointestinal peptide hormone which stimulates the motility of the gastrointestinal tract and induces a coordinated motility throughout the gastrointestinal tract in the fasting state and after intake of food.

The compounds of Formula I show motilin-like physiological effects in that they act as agonists for motilin receptors. Thus, the compounds of Formula I show pronounced stimulating effects in the gastrointestinal region and at the lower esophagus sphincter. In particular, they bring about an increased rate of gastric emptying, an increase in the stomach tone and a long-lasting increase in the resting tone of the esophagus sphincter. Because of their motilin-like activity profile, the substances are suitable for the treatment of pathological conditions which are associated with motility disturbances in the gastrointestinal tract and/or reflux of chyme from the stomach into the esophagus. Thus, the compounds of Formula I are indicated, for example, for gastroparesis with a very wide variety of causes, disturbances of the stomach tone, disturbances of gastric emptying and gastro-esophageal reflux, dyspepsia and postoperative motility disturbances.

The gastrointestinally effective properties of the compounds of Formula I can be demonstrated in standard pharmacological test methods in vitro and in vivo.

DESCRIPTION OF THE TEST METHODS

1. Determination of the binding capacity of the test substances to motilin receptors.

The affinity of the compounds of Formula I for motilin receptors is measured in vitro on a fraction of a tissue homogenate from rabbit antrum. The displacement of radioactively labelled iodinated motilin from motilin receptor binding by the test substances is determined.

The receptor binding studies are carried out by a modification of the method of Borman et al. (*Regulatory Peptides*, 15:143–153 (1986). To prepare the $^{125}$iodine-labelled motilin, motilin is iodinated enzymatically using lactoperoxidase in known manner, for example in analogy to the method described by Bloom et al., *Scand. J. Gastroenterol.*, 11:47–52 (1976).

To obtain the fraction of tissue homogenate used in the test from rabbit antrum, the antrum from which the mucosa have been removed is comminuted and homogenized in 10 times the volume of a cold homogenization buffer solution (50 mM tris-HCl buffer, 250 mM sucrose, 25 mM KCl, 10 mM $MgCl_2$, pH 7.4) with the addition of inhibitors (1 mM iodoacetamide, 1 μM pepstatin, 0.1 mM methylsulfonyl fluoride, 0.1 g/l trypsin inhibitor, 0.25 g/l bactracin) with a homogenizer at 1500 revolutions per minute for 15 sec. The homogenized is then centrifuged at 1000 g for 15 minutes, the resulting residue is washed four times with homogenization buffer solution and finally re-suspended in 0.9% strength sodium chloride solution (in a volume corresponding to 5 times the amount by weight of the antrum). The tissue fraction obtained in this way, which is referred to as "crude membrane preparation", is used for the test.

For the binding test, 200 μl of the crude membrane fraction (0.5–1 mg of protein) in 400 μl of a buffer solution A (50 mM tris-HCl buffer, 1.5% BSA, 10 mM $MgCl_2$, pH 8.0) are incubated with 100 μl of iodinated motilin diluted in buffer solution B (10 mM tris-HCl buffer, 1% BSA, pH 8) (final concentration 50 pM) at 30° C. for 60 min. The reaction is stopped by adding 3.2 ml of cold buffer solution B, and bound and non-bound motilin are separated from one another by centrifugation (1000 g, 15 minutes). The residue obtained as pellet after the centrifugation is washed with buffer solution B and counted in a gamma counter. The displacement studies are carried out by adding increasing amounts of the substance to be tested to the incubation medium. The test substance solutions employed are aqueous solutions which are prepared by suitable dilution of $60\times10^{-4}$ molar aqueous stock solutions. Test substances which are sparingly soluble in water are initially dissolved in 60% strength ethanol, and this solution is diluted with sufficient water for the ethanol concentration in the solution to be tested not to exceed 1.6% by volume. The $IC_{50}$ of the particular test substance is determined from the resulting measured data as that concentration which brings about 50% inhibition of the specific binding of the iodinated motilin to the motilin receptors. From this the corresponding $pIC_{50}$ value is calculated. The $pIC_{50}$ value determined by the preceding method for the substance of Example 1 was 7.85.

2. In vivo determination of the effect of the substances on the stomach tone.

The stomach tone plays an important role in gastric emptying. An increased stomach tone contributes to an increased rate of gastric emptying.

The influence of substances on the stomach tone is determined on beagles with the aid of a barostat which is connected to a plastic pouch in the stomach of the dog and permits measurement of volume or pressure in the stomach of the dog. With the barostat, the stomach volume is determined at a constant pressure in the stomach or the stomach pressure is determined at a constant volume in the stomach. When the stomach tone increases, a reduced stomach volume is detected at a given pressure, and an increased pressure at a given volume. In the test model used to investigate the increase in stomach tone effected by the substances, the change in stomach volume caused by the substances is measured at constant pressure. The stomach of the test animals is relaxed by intake of lipids, i.e. the stomach tone decreases, which causes the stomach volume to increase correspondingly. The reduction in % of the stomach volume which has been increased by administration of lipids which occurs after intake of the substance due to a re-increase in stomach tone is measured as a measurement of the stomach tone-increasing action of the substances. The substance of Example 1 in this test model in the maximum tolerable dose showed a reduction in the stomach volume increased after lipid administration by 69%.

Because of their effects in the gastrointestinal tract, the compounds of Formula I are suitable in gastroenterology as pharmaceuticals for larger mammals, especially humans, for the prophylaxis and treatment of motility disturbances in the gastrointestinal tract.

The doses to be used may differ between individuals and naturally vary depending on the nature of the condition to be treated and the form of administration. For example, parenteral formulations will generally contain less active substance than oral preparations. However, in general medicament forms with an active substance content of 1 to 100 mg per single dose are suitable for administration to larger mammals, especially humans.

As medicinal agents, the compounds of Formula I can be contained with conventional pharmaceutical auxiliary substances in pharmaceutical formulations such as, for example, tablets, capsules, suppositories or solutions. These pharmaceutical formulations can be produced by methods known per se using conventional solid vehicles such as, for example, lactose, starch or talcum or liquid diluents such as, for example, water, fatty oils or liquid paraffins, and using customary pharmaceutical auxiliary substances, for example tablet disintegrants, solubilizers or preservatives.

The following examples are intended to illustrate the invention in further detail without restricting its scope.

EXAMPLE 1

[(1'R),2R,3S,4S,5R,6R,9R,11R,12R,14R]-11-(1'-hydroxypropyl)-3-[(2,6-dideoxy-3-C-methyl-3-0-methyl-α-L-ribohexopyranosyl)-oxy]-5-[(3,4,6-trideoxy-3-(N-methyl-N-isopropylamino)-β-D-xylo-hexopyranosyl)-oxy]-2,4,6,8,11,14-hexamethyl-10,13,15-trioxatricyclo[$9.2.1.1^{9.6}$]-pentadecan-1-one (=mixture of isomers of the compound of Formula I, $R^1$=methyl).

A) Preparation of N-demethylerythromycin A.

20 g of erythromycin A (=27.2 mmole) and 11.2 g (=136.2 mmole) of sodium acetate were dissolved in 200 ml of an 8:2 methanol/water mixture. The solution was heated to 47° C.; Then 6.9 g (=136.2 mmole) of iodine were added. The pH value was maintained at 8 to 9 by adding dilute aqueous sodium hydroxide solution. After 3 hours, the reaction mixture was worked up by pouring it into a mixture of 11 of water and 20 ml of ammonium hydroxide solution. The reaction mixture was extracted with ethyl acetate, and the organic extract was washed with ammonium hydroxide-containing water and concentrated. The crude product remaining after removal of the solvent was recrystallized from acetone/ammonium hydroxide solution 50:3. Melting point 143–148° C.

B) Preparation of N-demethyl-8,9-anhydroerythromycin A 6,9-hemiketal (=compound of Formula V, $R^1$=methyl).

21 g of the product obtained in A) were dissolved in 110 ml of glacial acetic acid, and the solution was stirred at room temperature for 1 hour. The reaction mixture was then worked up by adding it dropwise to 400 ml of concentrated ammonium hydroxide solution with cooling in ice. The reaction mixture was extracted with ethyl acetate, the organic extract was washed with water, and the solvent was removed. The crude product remaining as residue was recrystallized first from ether and then from methanol. 14 g of pure product with a melting point of 145° C. were obtained.

C) Preparation of [2R(2'R,3'R),3S,4S,5R,6R,10R,11R]-11-(2',3'-dihydroxypent-2'-yl)-3-[(2,6-dideoxy-3-C-methyl-3-0-methyl-α-L-ribohexopyranosyl)-oxy]-5-[(3,4,6-trideoxy-3-methylamino-β-D-xylo-hexopyranosyl)-oxy]-2,4,6,8,10-pentamethyl-12,13-dioxabicyclo[8.2.1]-tridec-8-en-1-one (=compound of Formula III, $R^1$=methyl).

9.4 g (=13.4 mmole) of the product obtained in B) were boiled under reflux with 1.9 g (=13.4 mmole) of potassium carbonate in methanol for 2.5 hours. The reaction mixture was worked up by concentrating it, diluting with water and extracting with ethyl acetate. The crude product remaining after removal of the solvent was recrystallized from isopropanol. 7.1 g of pure product with a melting point of 199 to 200° C. were obtained, optical rotation $[\alpha]_D^{20}$: −31.6° (c=1, methanol).

D) Preparation of [2R(2'R,3'R),3S,4S,5R,6R,10R,11R]- 11-(2',3'-dihydroxypent-21-yl)-3-[(2,6-dideoxy-3-C-methyl-3-0-methyl-α-L-ribohexopyranosyl)-oxy]-5-[(3,4,6-trideoxy-3-(N-methyl-N-isopropylamino)-β-D-xylo-hexopyranosyl)-oxy]-2,4,6,8,10-pentamethyl-12,13-dioxabicyclo[8.2.1]-tridec-8-en-1-one (=compound of Formula II, $R^1$=methyl).

2 g (=2.8 mmole) of the product obtained in C) above were dissolved in methanol, and the pH value of the solution was adjusted to 4 by adding dilute hydrochloric acid solution. To the solution were added 2 g of a molecular sieve (calcium aluminum silicate, pore diameter 4 Å), an excess of acetone and 0.4 g (=6.4 mmole) of sodium cyanoborohydride. The reaction mixture was stirred for 12 hours. For working up, the molecular sieve was filtered out, the filtrate was concentrated, mixed with water and extracted with ethyl acetate. The crude product remaining as residue after concentration of the ethyl acetate extract was purified by column chromatography on silica gel (eluent ethyl acetate/methanol 95:5). 1.4 g of the purified product with a melting point of 130 to 134° C. were obtained, optical rotation $[\alpha]_D^{20}$: −32.8°.

E) Production of the title compound 30 g of the product obtained above in D) were added to 2250 ml water. Concentrated hydrochloric acid was added dropwise to the mixture, with stirring, until a pH value of 2–3 was reached. Then the reaction mixture was stirred for 7 hours at room temperature. For working up, concentrated ammonia solution was added to the reaction mixture until pH 11 was reached. Then the reaction mixture was extracted with dichloromethane. The organic extract was concentrated. The crude product remaining after concentration of the dichloromethane extract was purified by recrystallization from acetonitrile. 19.6 g of the title compound with a melting point of 181 to 183° C. were obtained, optical rotation $[\alpha]_D^{20}$: −52.2°.

Separation of isomers

The separation of the isomers was effected by semi-preparative high-performance liquid chromatography (abbreviated as HPLC) on a final column having the dimensions 300 mm (L)×7.8 mm (ID), manufactured by Waters.

The reversed-phase column material “Symmetry-Prep®” C18 (7 μm) was used. A mixture of 600 ml of an aqueous 0.05M $KH_2PO_4$ solution having a pH value of 6.0 (adjusted with a 1M NaOH solution) and 400 ml acetonitrile was used as eluent. With a retention time of 5.2 minutes, the 8R isomer was obtained. With a retention time of 6.8 minutes, the 8S isomer was obtained.

EXAMPLE 2

[(1'R),2R,3S,4S,5R,6R,9R,11R,12R,14R]-11-(1'-hydroxypropyl)-3-[(2,6-dideoxy-3-C-methyl-3-0-methyl-α-L-ribohexopyranosyl)-oxy]-5-[(3,4,6-trideoxy-3-(N-isopropylamino)-β-D-xylo-hexopyranosyl)-oxy]-2,4,6,8,11,14-hexamethyl-10,13,15-trioxatricyclo[9.2.1.1$^{9.6}$]-pentadecan-1-one (=mixture of isomers of the compound of Formula I, $R^1$=hydrogen).

A) Preparation of [2R(2'R,3'R),3S,4S,5R,6R,10R,11R]-11-(2',3'-dihydroxypent-2'-yl)-3-[(2,6-dideoxy-3-C-methyl-3-0-methyl-α-L-ribohexopyranosyl)-oxy]-5-[(3,4,6-trideoxy-3-(N-isopropylamino)-β-D-xylo-hexopyranosyl)-oxy]-2,4,6,8,10-pentamethyl-12,13-dioxa-bicyclo[8.2.1]-tridec-8-en-1-one.

A mixture of 7.3 g sodium methylate and 500 ml methanol was cooled to 0° C. under a nitrogen atmosphere. Then a solution of 20 g of the compound of Formula II ($R^1$=methyl) obtained in Example 1D) in 100 ml methanol was added thereto in drops. Then 34.1 g iodine were added in portions and the reaction mixture was kept at a temperature of 0 to 5° C. for 24 hours. For working up, the reaction mixture was poured into a solution of 58 g sodium thiosulfate and 48 ml concentrated ammonia solution in 1.5 liters of water. The aqueous phase was extracted four times with 100 ml of chloroform each time. The combined organic phases were washed once with a mixture of 5 ml concentrated ammonia solution and 100 ml water, dried over sodium sulfate and concentrated. The remaining residue was purified using column chromatography on silica gel. 0.5 g of purified product with a melting point of 147 to 155° C. were obtained, optical rotation $[\alpha]_D^{20}$: −26.2°.

B) Preparation of the title compound 1 g of the product obtained above was reacted according to the method described in Example 1E). 0.47 g of the title compound with a melting point of 201 to 209° C. were obtained, optical rotation $[\alpha]_D^{20}$: −45.8°.

EXAMPLE I

[(1'R),2R,3S,4S,5R,6R,9R,11R,12R,14R]-11-(1'-hydroxypropyl)-3-[(2,6-dideoxy-3-C-methyl-3-0-methyl-α-L-ribohexopyranosyl)-oxy]-5-[(3,4,6-trideoxy-3-(N-methyl-N-isopropylamino)-β-D-xylohexopyranosyl)-oxy]-2,4,6,8,11,14-hexamethyl-10,13,15-trioxatricyclo-[9.2.1.$^{9.6}$]-pentadecan-1-one (=isomer mixture of the compound of Formula I, $R^1$=methyl) 20 mg Cornstarch 60 mg Lactose 135 mg Gelatin (as 10% strength solution) 6 mg The active compound, the cornstarch and the lactose were thickened with the 10% strength gelatin solution. The paste was comminuted, and the resulting granules were placed on a suitable metal sheet and dried at 45° C. The dried granules were passed through a comminuting machine and mixed with the following other auxiliary substances in a mixer:

Talc 5 mg

Magnesium stearate 5 mg

Maize starch 9 mg and then compressed to 240 mg tablets.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A [(1'R),2R,3S,4S,5R,6R,9R,11R,12R,14R]-11-(1'-hydroxypropyl)-2,4,6,8,11,14-hexamethyl-10,13,15-trioxatricyclo[9.2.1.1$^{9.6}$]-pentadecan-1-one compound corresponding to formula I:

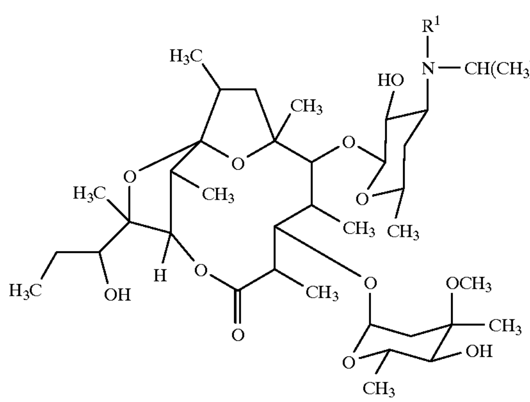

wherein $R^1$ denotes methyl or hydrogen, or a stable and physiologically acceptable acid addition salt thereof.

2. A compound according to claim 1, wherein $R^1$ is methyl.

3. A pharmaceutical composition comprising a pharmacologically effective amount of a compound according to claim 1, and at least one pharmaceutical carrier or adjuvant.

4. A method of preparing a [(1'R),2R,3S,4S,5R,6R,9R,11R,12R,14R]-11-(1'-hydroxypropyl)-2,4,6,8,11,14-hexamethyl-10,13,15-trioxatricyclo[9.2.1.1$^{9,6}$]-pentadecan-1-one compound corresponding to formula I:

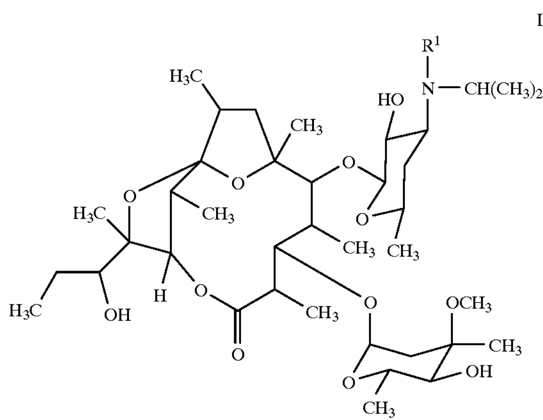

wherein $R^1$ denotes methyl or hydrogen, said method comprising treating a [2R(2'R,3'R),3S,4S,5R,6R,10R,11R]-11-(2',3'-dihydroxypent-2'-yl)-2,4,6,8,10-pentamethyl-12,13-dioxabicyclo[8.2.1]-tridec-8-en-1-one compound corresponding to formula II:

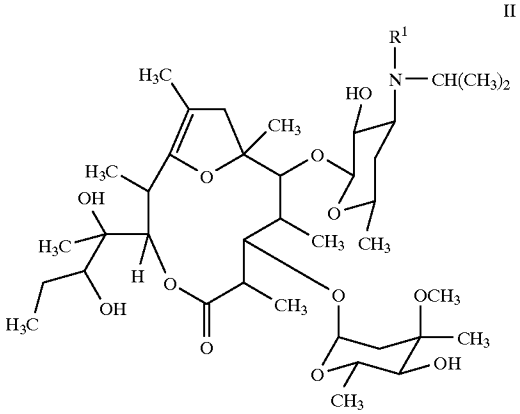

wherein $R^1$ has the above meaning, with acid to convert said compound of formula II into a compound of Formula I.

5. A method according to claim 4, wherein $R^1$ initially denotes hydrogen, further comprising the step of introducing a methyl group $R^1$ into the compound of Formula I to obtain a product in which $R^1$ is methyl.

6. A method according to claim 4, wherein $R^1$ initially denotes a methyl group, further comprising the step of cleaving off said methyl group, whereby a product is obtained in which $R^1$ is hydrogen.

7. A method according to claim 4, further comprising the step of treating an acid addition salt of a compound of formula I with a base to obtain a free base corresponding to Formula I.

8. A method according to claim 4, further comprising the step of treating a free base of formula I with a physiologically acceptable acid to obtain a physiologically acceptable acid addition salt thereof.

* * * * *